US00PP11273P

United States Patent [19]

Kordes

[11] Patent Number: Plant 11,273

[45] Date of Patent: Mar. 7, 2000

[54] FLORIBUNDA ROSE PLANT NAMED 'KORENON'

[75] Inventor: Wilhelm Kordes, Sparrieshoop, Germany

[73] Assignee: Bear Creek Gardens, Inc., Medford, Oreg.

[21] Appl. No.: 08/984,759

[22] Filed: Dec. 4, 1997

[51] Int. Cl.[7] ..... A01H 5/00

[52] U.S. Cl. ..... Plt./149

[58] Field of Search ..... Plt./27, 19, 28, Plt./20, 11, 22, 141, 142, 148, 149, 150, 130, 131, 138, 139

*Primary Examiner*—Howard J. Locker

*Attorney, Agent, or Firm*—Klarquist Sparkman Campbell Leigh & Whinston, LLP

[57] ABSTRACT

Floribunda rose plant having few thorns and good production of unusual pink colored flowers having long vase life and good shipping qualities.

1 Drawing Sheet

The present invention relates to a new and distinct variety of rose plant of the floribunda class which was originated by me by crossing the variety 'KORokis' (not patented), with an unnamed seedling.

The primary objective of this breeding was to produce a new rose variety having the excellent vase life, good production and very good shipping ability of the cut flowers of the female parent combined with the good production, good vase life, and thick petals of the unnamed male breeding line. The objective was substantially achieved, along with other desirable improvements, as evidenced by the following unique combination of characteristics that are outstanding in the new variety and that distinguish it from its parents, as well as from all other varieties of which I am aware:

1. Very unusual pink color;
2. Long vase life;
3. Good shipping ability;
4. High production;
5. Very few thorns.

KORenon is a pink floribunda cut rose with production of 200 or more stems per square meter of greenhouse (28–30 stems per plant per year).

Asexual reproduction of this new variety by budding, as performed at Sparrieshoop, Germany and Wasco, Calif., shows that the foregoing and all other characteristics and distinctions come true to form and are established and transmitted through succeeding propagtations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORokis (unpatented).

*Pollen parent.*—Unnamed.

Classification:

*Botanical.*—Rosa hybrida.

*Commercial.*—Floribunda.

FLOWER

Observations made from specimens grown in a greenhouse environment at Sparrieshoop, Germany and Somis, Calif. from January, 1996–September 1997.

Blooming habit: Continuous.

Bud:

*Size.*—One and one-half inches long when the petals start to unfurl.

*Form.*—The bud form is long, pointed ovoid.

*Color.*—When sepals first divide, bud color is Red Group 47C. When half blown, the outer half of the upper sides of the petals are Red Group 47C, the inner half is close to Orange-Red Group 32D; and the outer two-thirds of the lower sides of the petals are Red Group 47D, the inner one-third is Orange-Red Group 35D.

*Sepals.*—Color: Yellow-Green Group 146C. Surface texture: Covered in fine hairs. There are three lightly appendaged sepals. There are two unappendaged sepals with hairy edges.

*Receptacle.*—Color: Green Group 146C. Shape: Funnel. Size: Medium (7/16" long×7/16" wide). Surface: Smooth.

*Peduncle.*—Length: Short (2½" to 2¾"). Surface: Smooth. Color: Green Group 137C. Strength: Stiff, erect.

Bloom:

*Size.*—Medium. Average open size is three and one-half to four inches.

*Borne.*—Singly.

*Stems.*—Medium (20–24"), strong.

*Form.*—When first open: High centered. Permanence: Retains its form to the end; outer petals curl back.

*Petalage.*—Number of petals under normal conditions: 30–35.

*Color.*—The outer half of the upper sides of the petals are Red Group 47C, the inner half of the petal is close to Orange-Red Group 32D. The outer two-thirds of the reverse sides of the petals are Red Group 47D, the inner one-third is Orange Red Group 35D. The base of each petal has a small (¼"×3/16"), yellow half moon at the point of attachment. The major color on the upper sides is Red Group 47C.

*Variegations.*—Occasional greenish-white streak on the guard petals.

*Discoloration.*—At the end of the first day: No change. At the end of the third day: No change. Color is stable.

*Fragrance.*—Slight.

Petals:

*Texture.*—Thick, leathery.

*Shape.*—Round.

*Form.*—Tips slightly recurved.

*Arrangement.*—Imbricated. Petaloids in the center are few, one or two when present, and a majority of flowers have no petaloids. Petaloids observed were Red Group 47D in coloration and about 9 mm long and 3 mm wide.

*Persistence.*—Drop off cleanly.

*Lastingness.*—On the plant: Long (seven to eight days). As a cut flower: Long (ten to twelve days).

Reproductive parts:

*Anthers.*—Size: Medium. Quantity: Many. Color: Yellow. Arrangement: Regular around styles.

*Filaments.*—Color: Reddish brown.

*Pollen.*—Color: Gold yellow.

*Styles.*—Color: Reddish.

*Stigmas.*—Color: Greenish-white.

Plant:

*Form.*—Bush.

*Growth.*—Very vigorous; upright; branching; Height at six months growth in a Somis, Calif. greenhouse is six feet and width three and one-half feet. In the greenhouse, trained as a cut rose, the plant is somewhat like a hybrid tea in that it flowers one bud to a stem on fairly long stems. However, the buds are fairly small, and the open flower is too small to be classified as a hybrid tea. It is sold as an intermediate in cut flower channels. Growing in the field, the plant has the short, well-branched clustering habit of a floribunda.

Foliage:

*Number of leaflets on normal mid-stem leaves.*—Five.

*Size.*—Large (6"×4½").

*Quantity.*—Abundant.

*Color.*—New foliage: Upper and lower surface: Greyed-Purple Group 183A. Old foliage: Upper surface: Green Group 139A. Lower surface: Green Group 139C when young (one to three weeks) but when fully expanded has a caste of Greyed-Purple 184B.

*Shape.*—Broadly oval.

*Texture.*—Upper side: Leathery.

*Edge.*—Serrated.

*Serration.*—Single, small.

*Petiole rachis.*—Color: Reddish.

*Petiole underside.*—Smooth with occasional prickles.

*Stipules.*—Medium (½"); serrated, bearded.

*Disease resistance.*—Resistant to mildew under normal growing conditions at Sparrieshoop, Germany and Somis, Calif.

Wood:

*New wood.*—Color: Greyed Orange 176A. Bark: Smooth.

*Old wood.*—Color: Green 136B. Bark: Smooth.

Prickles:

*Quantity.*—On main canes from base: Few (1 per 3" of stem). On laterals from main canes: Few (0–3 thorns per stem).

*Form.*—Short (¼"); hooked slightly downward.

*Color when young.*—Greyed Orange 176B. When mature, Greyed Orange 165C.

Small prickles:

*Quantity.*—On main stalks: None: On laterals: None.

I claim:

1. A new and distinct variety of rose plant of the floribunda class, substantially as herein shown and described, characterized particularly as to novelty by very few thorns, unusual pink color, long vase life, good shipping qualities, and high production.

* * * * *

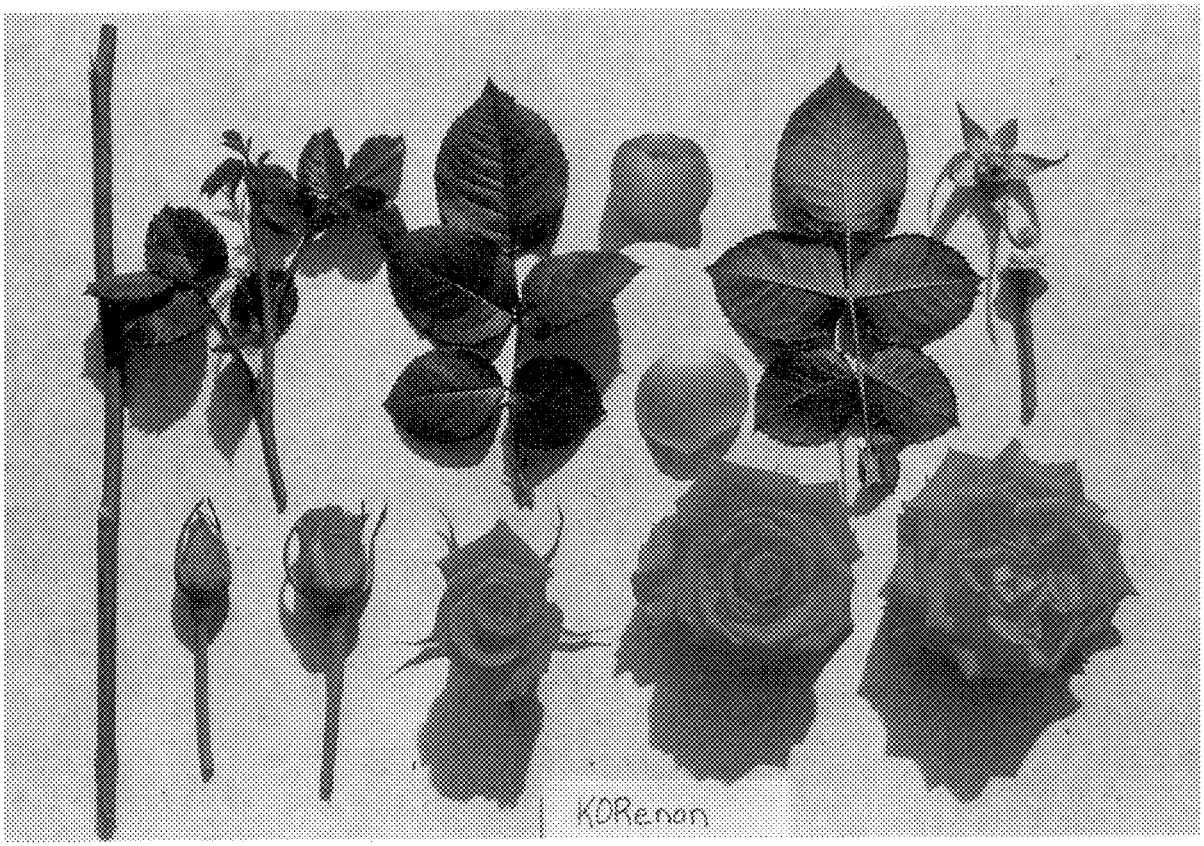
KDRenan